US008389263B2

(12) United States Patent
Daunert et al.

(10) Patent No.: US 8,389,263 B2
(45) Date of Patent: Mar. 5, 2013

(54) SPORES FOR THE STABILIZATION AND ON-SITE APPLICATION OF BACTERIAL WHOLE-CELL BIOSENSING SYSTEMS

(76) Inventors: Sylvia Daunert, Coral Gables, FL (US); Sapna K. Deo, Fishers, IN (US); Patrizia Pasini, Lexington, KY (US); Amol Date, Baltimore, MD (US)

(*) Notice: Subject to any disclaimer, the term of this patent is extended or adjusted under 35 U.S.C. 154(b) by 245 days.

(21) Appl. No.: 12/676,302

(22) PCT Filed: Sep. 10, 2008

(86) PCT No.: PCT/US2008/075865
§ 371 (c)(1),
(2), (4) Date: Aug. 20, 2010

(87) PCT Pub. No.: WO2009/036070
PCT Pub. Date: Mar. 19, 2009

(65) Prior Publication Data
US 2010/0304379 A1 Dec. 2, 2010

Related U.S. Application Data

(60) Provisional application No. 60/971,146, filed on Sep. 10, 2007.

(51) Int. Cl.
*C12N 1/00* (2006.01)
*C12N 1/12* (2006.01)
*C12N 1/20* (2006.01)
*C12N 3/00* (2006.01)

(52) U.S. Cl. .............. 435/242; 435/243; 435/252.1; 435/252.31; 435/252.7

(58) Field of Classification Search .................. None
See application file for complete search history.

(56) References Cited

U.S. PATENT DOCUMENTS

| 5,614,375 | A | 3/1997 | Citri |
| 5,776,681 | A | 7/1998 | Virta et al. |
| 5,972,638 | A | 10/1999 | Burlaage et al. |
| 6,017,722 | A | 1/2000 | Becvar |
| 6,110,661 | A | 8/2000 | Lajoie |
| 6,117,643 | A | 9/2000 | Simpson et al. |
| 6,210,910 | B1 | 4/2001 | Walt et al. |
| 6,228,574 | B1 | 5/2001 | Rotman |
| 6,329,160 | B1 | 12/2001 | Schneider |
| 6,340,572 | B1 | 1/2002 | Becvar |
| 6,377,721 | B1 | 4/2002 | Walt et al. |
| 6,498,137 | B1 * | 12/2002 | Schalitz et al. ............ 510/530 |
| 6,544,729 | B2 | 4/2003 | Sayler et al. |
| 6,596,496 | B1 | 7/2003 | Rotman |
| 6,638,752 | B2 | 10/2003 | Contag et al. |
| 6,872,539 | B2 | 3/2005 | Rotman |
| 7,208,286 | B2 | 4/2007 | Simpson et al. |
| 7,214,505 | B1 | 5/2007 | Cooper et al. |
| 7,267,993 | B2 | 9/2007 | Pentrenki et al. |
| 2002/0028445 | A1 | 3/2002 | Bercher |
| 2002/0086424 | A1 | 7/2002 | Contag et al. |
| 2003/0008337 | A1 | 1/2003 | Rotman |
| 2003/0027241 | A1 | 2/2003 | Sayler et al. |
| 2004/0063189 | A1 | 4/2004 | Walter |
| 2004/0115713 | A1 | 6/2004 | Laing |
| 2004/0115786 | A1 | 6/2004 | Laing |
| 2004/0171065 | A1 | 9/2004 | Kim et al. |
| 2004/0235003 | A1 | 11/2004 | Contag et al. |
| 2005/0147962 | A1 | 7/2005 | Wagstrom et al. |
| 2005/0176096 | A1 | 8/2005 | Kwon et al. |
| 2005/0255444 | A1 | 11/2005 | Van Der Meer |
| 2005/0272105 | A1 | 12/2005 | Levon et al. |
| 2006/0073539 | A1 | 4/2006 | Wikswo et al. |
| 2006/0292581 | A1 | 12/2006 | Laing |
| 2010/0291566 | A1 | 11/2010 | Daunert et al. |
| 2010/0304379 | A1 | 12/2010 | Daunert et al. |
| 2011/0117661 | A1 | 5/2011 | Daunert et al. |
| 2011/0229415 | A1 | 9/2011 | Daunert et al. |

FOREIGN PATENT DOCUMENTS

| WO | WO0132911 | 5/2001 |
| WO | WO2005028654 | 3/2005 |
| WO | WO2006083288 | 8/2006 |
| WO | WO2006105801 | 10/2006 |
| WO | WO2009021026 | 2/2009 |
| WO | WO2009021039 | 2/2009 |
| WO | WO2009021052 | 2/2009 |
| WO | WO2009036070 | 3/2009 |
| WO | WO2009036081 | 3/2009 |

OTHER PUBLICATIONS

Sato, et al., "The ars operon in the skin element of *Bacillus subtilis* confers resistance to arsenate and arsenite." Journal of Bacteriology. Apr. 1998; 180(7): 1655-1661.
Harms, et al., "Whole-cell living biosensors: are they ready for environmental application?" Appl Microbiol Biotechnol. 2006; 70: 273-280.
Daunert, et al., Chem. Rev. 2000, 100, 2705-2738.
Belkin, S. Curr. Opin. Microbiol 2003, 6, 206-212.
Gu, M. B.; et al., Adv. Biochem. Engin./Biotechnol. 2004, 87 269-305.
Standing, et al., FEMS Microbial. Lett. 2003, 220,35-39.
Kumari, et al., Anal. Chem. 2006, 78, (22), 7603-7609.
Feliciano, et al., Photoproteins as reporters in whole-cell sensing. In Photoproteins in Bioanalysis, Daunert, S.; Deo, S. K., Eds. Wiley VCH: Weinheim, 2006, pp. 131-154.
Galluzzi, et al., Comb. Chem. High Throughput Screen. 2006, 9, (7), 501-14.
Yagi, K. Appl. Microbiol. Biotechnol. 2007, 73,1251-1258.
Erbe, et al., Nucleic Acids Res. 1995, 23, 2472-2478.
Sorensen, et al., Curr. Opinion. Biotechnol. 2006, 17, 11-16.
Turner, et al., Anal. Chem. 2007, published on web Jun. 30, 2007.
Shetty, et al., Biotechnol. Bioeng. 2004, 88, (5), 66470.
Ramanathan, et al., Anal. Chim. Acta 1998, 369, 189-95.
Stocker, et al., Environ. Sci. Technol. 2003, 37, (20), 4743-50.
Premkumar, et al., Anal. Chim. Acta 2002, 462,11-23.
Polyak, et al., Sens. Actuators B Chem. 2001, 74,18-26.
Mbeunkui, et al., Appl. Microbiol. Biotechnol. 2002, 60, 306-312.
Bjerketorp, et al., J. Curr. Opin. Biotechnol. 2006, 17, 43-49.
Nicholson, W. L. Cell. Mol. Life. Sci. 2002, 59, 410-416.
Moir, et al., Cell. Mol. Life Sci. 2002, 59, 403-409.
Turner, et al., Nucleic Acids Res. 1996, 24, 3714-3721.
Abernathy, et al., Environ. Health Perspect. 1999, 107, 593-97.
Black, M. M. J. Nutr. 2003, 133 1473-76.

* cited by examiner

*Primary Examiner* — Albert Navarro
(74) *Attorney, Agent, or Firm* — Stites & Harbison PLLC; Mandy Wilson Decker (57) ABSTRACT

The presently-disclosed subject matter is directed to biosensors comprising spore-forming bacterial cells and/or spores generated therefrom, a recognition unit within each spore-forming cell for binding an analyte of interest, and a reporter molecule within each spore-forming cell for detecting binding of the analyte of interest, wherein the reporter molecule generates a detectable signal upon binding of the analyte by the recognition element. The presently-disclosed subject matter further provides methods of using the biosensors and systems and kits including the biosensors.

11 Claims, 6 Drawing Sheets

SPORES FOR THE STABILIZATION AND ON-SITE APPLICATION OF BACTERIAL WHOLE-CELL BIOSENSING SYSTEMS

RELATED APPLICATIONS

The presently disclosed subject matter claims the benefit of U.S. Provisional Patent Application Ser. No. 60/971,146, filed Sep. 10, 2007; the disclosure of which is incorporated herein by reference in its entirety.

STATEMENT REGARDING FEDERALLY SPONSORED RESEARCH

The presently-disclosed subject matter was made with government support under Grant Number 0416553 awarded by the National Science Foundation. The government has certain rights in the presently-disclosed subject matter.

TECHNICAL FIELD

The presently disclosed subject matter relates to biosensors for detecting analytes of interest. In particular, the presently disclosed subject matter relates to biosensors comprising spore-forming bacterial cells and/or spores generated from the spore-forming bacterial cells.

BACKGROUND

Whole-cell sensing systems employ genetically engineered living cells that contain biospecific recognition elements for the detection of analytes of interest. In bacterial operon-based whole-cell sensing systems, the sensing element is comprised of a regulatory gene encoding a regulatory protein and a specific operator/promoter (O/P) sequence of DNA. The regulatory protein is capable of recognizing the analyte and controlling expression of a reporter gene that is placed under transcriptional control of the O/P. Upon binding the target analyte, the regulatory protein activates gene transcription, with subsequent expression of the reporter protein leading to the generation of a detectable signal. The reporter gene is expressed in a concentration dependent manner and calibration plots can be constructed by relating the signal generated with the concentration of analyte.

Whole-cell sensing systems have been employed in a variety of environmental bioassays, as well as in biotechnology, pharmacology, and clinical chemistry applications. Numerous whole-cell sensing systems have been developed for environmental monitoring purposes. These include biosensors for the detection of toxic compounds such as mercury, arsenic, cadmium, lead, zinc, and several organic pollutants present in different types of environmental samples.[1-3] Recently, they have also been used for monitoring the bioavailability of chemicals such as nitrogen, phosphorus, and carbon in soil.[4] Additionally, whole-cell sensing systems have been developed for the detection of biomolecules, including sugars, drugs, and quorum sensing signal molecules.[5-7] Various aspects of the construction of genetically engineered microorganisms and their application as biosensors in various fields have been discussed in recent reviews, which are incorporated herein by reference in their entireties.[1,3,8-10] These bacterial sensing systems can provide an inexpensive and simple way to selectively, sensitively and rapidly detect very low levels of analytes. Additionally, they can supply important information about the bioavailability and activity of the analyzed compounds.

Although these systems and methods are promising, improvements are needed, especially for long-term storage in unfavorable conditions. Accordingly, there remains a need in the art for development of whole-cell biosensors that function satisfactorily after long-term storage, even under harsh environmental conditions.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments of the presently-disclosed subject matter, a biosensor is provided. The biosensor comprises a spore-forming bacterial cell, wherein the cell can generate one or more spores capable of being germinated to thereby reproduce the spore-forming bacterial cell. The biosensor further comprises a recognition element within the spore-forming bacterial cell for binding an analyte of interest. In addition, the biosensor comprises a reporter molecule within the spore-forming bacterial cell for detecting binding of the analyte of interest, wherein the reporter molecule generates a detectable signal upon binding of the analyte by the recognition element. The presently-disclosed subject matter further includes a spore generated from the spore-forming bacterial cell of the biosensor.

In some embodiments, the spore-forming bacterial cell is a *Bacillus* sp. bacterial cell, such as for example from *Bacillus subtilis* or *Bacillus megaterium*, or a *Clostridium* sp. bacterial cell.

In some embodiments, the spore-forming bacterial cell is a transformed bacterial cell. For example, in some embodiments, the bacterial cell comprises a heterologous polynucleotide expression cassette comprising a promoter operatively linked to a nucleotide sequence encoding the reporter molecule. In some embodiments, the recognition element is a regulatory peptide having binding affinity for the promoter. The regulatory peptide can bind the promoter and inhibit expression of the reporter molecule. Binding of the analyte of interest by the regulatory peptide can release binding of the regulatory peptide to the promoter, thereby allowing expression of the reporter molecule and generation of the detectable signal. In some particular exemplary embodiments, the regulatory peptide comprises an ArsR peptide, an SmtB peptide, an HbpR peptide, an AraC peptide, or a functional fragment thereof. Further, in some particular exemplary embodiments, the expression cassette is a plasmid selected from the group consisting of pMUTin-23 and pSD202. the reporter molecule comprises a peptide selected from the group consisting of β-galactosidase and green fluorescent protein.

In some embodiments, the analyte of interest is a toxic compound or a biomolecule. Exemplary toxic compounds of interest include, but are not limited to e.g., mercury, cadmium, arsenic, zinc, lead, and organic pollutants. Exemplary biomolecules of interest include, but are not limited to sugars, peptides, or organic compounds, including drugs.

The presently-disclosed subject matter further provides in some embodiments, a system for detecting an analyte of interest. The system comprises a biosensor as disclosed herein comprising a spore-forming bacterial cell (and/or a spore generated from the spore-forming bacterial cell), a recognition element, and a reporter molecule. The system further comprises a substrate supporting the spore-forming bacterial cell and/or the spore.

In some embodiments, the system further comprises a signal reader for detecting the signal generated by the reporter molecule. In some embodiments, the substrate is a microfluidic platform, a container, or a paper strip.

The presently-disclosed subject matter still further provides in some embodiments, a kit for detecting an analyte of interest. The kit comprises a biosensor as disclosed herein and instructions for using the biosensor.

The presently-disclosed subject matter still further provides in some embodiments, a method of detecting an analyte of interest. The method comprises contacting a test sample suspected of containing the analyte of interest with a biosensor as disclosed herein, wherein the biosensor comprises a spore-forming bacterial cell which can generate one or more spores capable of being germinated to thereby reproduce the spore-forming bacterial cell. The method further comprises determining whether a detectable signal is produced by the biosensor to thereby detect the analyte of interest. In some embodiments, the method first comprises germinating a spore into a spore-forming bacterial cell as disclosed herein, which can be utilized as a biosensor of the presently-disclosed subject matter. In some embodiments, the test sample is an environmental sample or a biological sample.

Accordingly, it is an object of the presently disclosed subject matter to provide biosensors for detecting analytes of interest. This object is achieved in whole or in part by the presently disclosed subject matter.

An object of the presently disclosed subject matter having been stated hereinabove, and which is achieved in whole or in part by the presently disclosed subject matter, other objects and advantages will become evident to those of ordinary skill in the art after a study of the following description of the presently disclosed subject matter, figures, and non-limiting examples.

DETAILED DESCRIPTION

The details of one or more embodiments of the presently disclosed subject matter are set forth in the accompanying description below. Other features, objects, and advantages of the presently disclosed subject matter will be apparent from the detailed description, Appendix, and claims. All publications, patent applications, patents, and other references mentioned herein are incorporated by reference in their entirety.

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The present inventors have successfully developed a number of whole-cell sensing systems that have found applications in a variety of fields.[3,5,7,11-12] The previous work of the inventors and others with whole-cell biosensors gave insight into these systems to identify their advantages, as well as their limitations. Moreover, the inventors postulated that the utility of whole-cell sensing systems could further be enhanced by packaging them in an appropriate manner that increases their shelf life and improves their effective use for on-site monitoring. To that end, certain requirements can be desirable to meet. Whole-cell-based biosensors possess the characteristics required for field analysis in that they are sensitive, reproducible, robust, and easy to use.[13,14] Portability, preservation, and long-term storage of the sensor bacteria can also be desirable features for on-site applications. Methods for incorporating the biosensing cells into transportable devices, such as sol-gel encapsulation, immobilization on microtiter plates and attachment onto optic fiber tips, have been developed.[15-17] Moreover, various preservation techniques have been employed to maintain the bacterial sensing cells viable and active, which include freeze-drying, vacuum-drying, continuous cultivation, and immobilization in organic and inorganic biocompatible polymers.[18]

Whole-cell sensing systems based on living genetically engineered bacteria are known to have high sensitivity, selectivity, and rapid response times. While these systems have found applications in biomedical and environmental analyses, their limited shelf-life and transportability still restrict their use for on-site monitoring of analytes. To that end, the presently-disclosed subject matter provides new biosensors, and systems, kits, and methods of using same, for the long-term preservation, storage, and transport of whole-cell biosensing systems that are based on bacterial spores, a dormant form of life.

In some embodiments of the presently-disclosed subject matter, a biosensor comprising a spore-forming bacterial cell is provided. That is, the bacterial cell can generate one or more spores capable of being germinated to thereby reproduce the spore-forming bacterial cell, which allows for the long-term storage and easy transportation of the biosensor in spore form. In some embodiments, the biosensor further includes a recognition element within the spore-forming bacterial cell for binding an analyte of interest. In some embodiments, the biosensor further includes a reporter molecule within the spore-forming bacterial cell for detecting binding of the analyte of interest and then generating a detectable signal upon binding of the analyte by the recognition element.

In some embodiments, the spore-forming bacterial cell is a transformed bacterial cell. The terms "transformed", "transgenic", and "recombinant" refer to a cell, such as a bacterial cell, into which a heterologous nucleic acid molecule has been introduced. The nucleic acid molecule can be stably integrated into the genome of the cell, and/or the nucleic acid molecule can be present as an extrachromosomal molecule (e.g., a plasmid). Such an extrachromosomal molecule can be auto-replicating. Transformed cells are understood to encompass not only the end product of a transformation process, but also transgenic progeny thereof, including vegetative cells and spores. A "non-transformed," "non-transgenic", or "non-recombinant" host refers to a wild type organism, e.g., a cell, which does not contain the heterologous nucleic acid molecule. For example, in some embodiments, the bacterial cell has been transformed with a plasmid comprising a heterologous polynucleotide expression cassette comprising a promoter operatively linked to a gene encoding the reporter molecule. In some embodiments, the plasmid is a pMUTin-23 or a pSD202 plasmid (see FIG. 1).

The term "expression cassette" refers to a nucleic acid molecule capable of directing expression of a particular nucleotide sequence in an appropriate host cell, comprising a promoter and/or other regulatory sequences operatively linked to the nucleotide sequence of interest which can be operatively linked to termination signals. It also typically comprises sequences required for proper translation of the nucleotide sequence. The coding region usually encodes a polypeptide of interest but can also encode a functional RNA of interest. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides. In contrast, a "homologous" nucleic acid (or amino acid) sequence is a nucleic acid (or amino acid) sequence naturally associated with a host cell into which it is introduced.

The terms "associated with", "operably linked", and "operatively linked" refer to two nucleic acid sequences that are related physically or functionally. For example, a promoter or regulatory DNA sequence is said to be "operatively linked with" a DNA sequence that encodes an RNA or a polypeptide if the two sequences are operatively linked, or situated such that the regulator DNA sequence will affect the expression level of the coding or structural DNA sequence.

In some embodiments of the presently-disclosed subject matter, the biosensor recognition element is a regulatory peptide having binding affinity for the promoter operably linked to the gene encoding the reporter molecule. In these embodiments, when the regulatory peptide binds the promoter, it can inhibit expression of the reporter molecule by blocking effective transcription, thus effectively preventing the reporter molecule from being produced and from then generating a detectable signal. However, in the presence of the analyte of interest, the regulatory peptide binds the analyte and releases from the promoter (e.g., due to a conformational change in the regulatory peptide), thereby allowing for expression of the reporter molecule, which in turn results in generation of the detectable signal.

As used herein, the term "binding affinity" refers to an interaction between at least two components in a system, e.g., a recognition element and an analyte or a recognition element (e.g., a regulatory peptide) and a polynucleotide expression cassette promoter. The interaction between two or more compositions or components can be identified as specific or non-specific. A "high binding affinity" can be a specific interaction between compositions or components. In some embodiments, a high binding affinity is found when the equilibrium dissociation constant ($K_d$) is less than about 100 nM, 75 nM, 50 nM, 25 nM, 20 nM, 10 nM, 5 nM, or 2 nM. A "low binding affinity" can be a non-specific interaction between compositions or components. In some embodiments, a low binding affinity is found when the equilibrium dissociation constant ($K_d$) is greater than about 100 nM, 125 nM, 150 nM, 175 nM, 200 nM, 225 nM, or 250 nM.

In some exemplary embodiments, the regulatory peptide can be an ArsR peptide, an SmtB peptide, an HbpR peptide (derived from *Pseudomonas azelaica* strain HBP1, as disclosed in Turner et al. (2007) *Anal. Chem.*, 79:5740-5745, herein incorporated by reference in its entirety), an AraC peptide, or a functional fragment thereof The regulatory peptides can in some embodiments be encoded for on the same heterologous nucleic acid molecule as the expression cassette. The ArsR peptide binds arsenic with specificity, the HbpR peptide binds hydroxylated polychlorinated biphenyl molecules (OH—PCBs) with specificity, the AraC binds L-arabinose with specificity, and the SmtB binds zinc with specificity. Each of these proteins undergoes a conformational change when binding the analyte that results in its release from the promoter/operon operator, thereby permitting effective expression of the reporter molecule.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "fragment" refers to a sequence that comprises a subset of another sequence. When used in the context of a nucleic acid or amino acid sequence, the terms "fragment" and "subsequence" are used interchangeably. A fragment of a nucleic acid sequence can be any number of nucleotides that is less than that found in another nucleic acid sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleic acid sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc.

A fragment can also be a "functional fragment," in which the fragment retains a specific biological function of the nucleic acid sequence or amino acid sequence of interest. For example, a functional fragment of a regulatory peptide can include, but is not limited to, a DNA binding domain and an analyte binding domain.

In some embodiments, the reporter molecule comprises a peptide selected from the group consisting of: β-galactosidase; green fluorescent protein, including all known variants thereof; red fluorescent protein; aequorin, including all known variants thereof; obelin, including all known variants thereof; a bacterial luciferase; a firefly luciferase; a renilla luciferase; and a railroad worm luciferase. In some embodiments, the analyte of interest is a toxic compound (e.g., mercury, cadmium, arsenic, zinc, lead, organic pollutants including PCBs and OH—PCBs, etc.) or a biomolecule (e.g., sugars (including L-arabinose), peptides, or organic compounds, including drugs and bacterial signaling molecules).

As non-limiting specific examples of the presently-disclosed biosensors, spore-forming bacteria, such as *Bacillus subtilis*, *Bacillus megaterium*, and *Clostridium* sp. are provided (see Examples for details), that have been developed as luminescent sensing systems for a variety of analytes, including arsenic and zinc. The vegetative "sensing cells" can be converted to spores, which can then be "revived" (germinated) at a later time to generate viable and metabolically active vegetative cells. The presently-disclosed spore-based sensing systems retain their analytical performance, in terms of detection limit, dynamic range, and reproducibility, after storage at room temperature for extended periods of time (e.g., at least six months or longer), as well as after multiple cycles (e.g., three cycles) where the cells are alternated between being dormant or active (i.e., sporulation/germination cycles). The ability to cycle the sensing cells between active and dormant states prolongs the cell's lifetimes and increases their robustness and ruggedness, thus making them more amenable for field applications.

The small size and hardiness of the cell sensors when in spore form allows for their easy transport and incorporation in miniaturized portable devices. Thus, The presently-disclosed novel strategy can facilitate expansion of the use of whole-cell biosensors for on-site sensing not only in mild environments, but also in harsh environments and locations where there is no easy access to a laboratory, e.g., in developing countries. As such, in some embodiments, the presently-disclosed subject matter provides systems incorporating the presently-disclosed biosensors and methods of using same.

As such, in some embodiments of the presently-disclosed subject matter, a system for detecting an analyte of interest is provided. In some embodiments, the system comprises, a spore-forming bacterial cell biosensor as disclosed herein, spores generated from the spore-forming bacterial cells, or both, including a recognition element and a reporter molecule. The system further comprises a substrate supporting the spore-forming bacterial cell; and a signal reader for detecting the signal generated by the reporter molecule. In some embodiments, for example, the substrate can be a microfluidic platform, a container (e.g., a test tube or a well of a microtiter plate), an optic fiber, or a paper strip.

Figure 7:
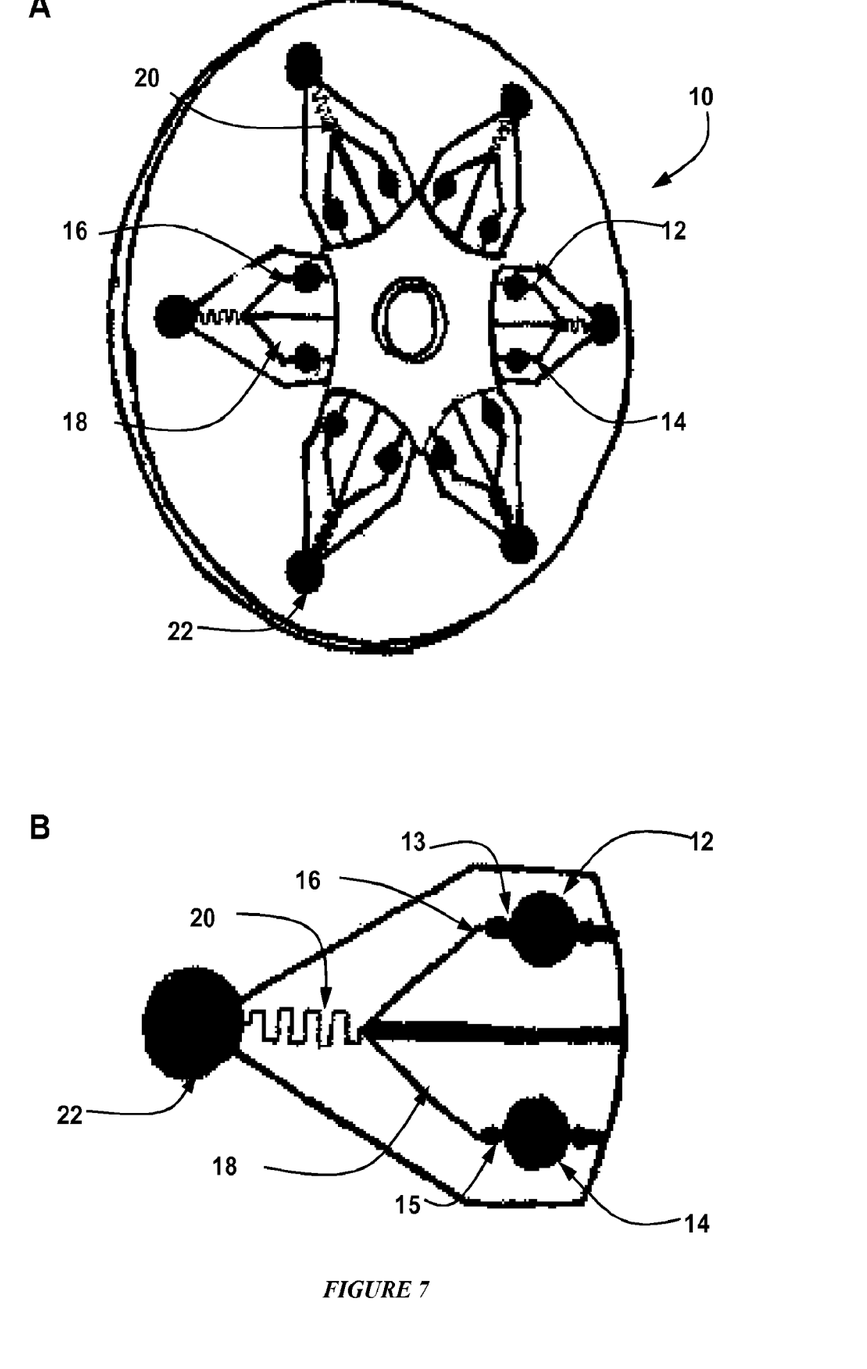
FIGS. 7A and 7B are schematic drawings of a microfluidics platform and a component thereof, respectively, for use with the biosensors disclosed herein.

As one exemplary embodiment of a microfluidic platform system using biosensors comprising spores disclosed herein, the presently-disclosed subject matter provides an effective packaging method for the storage, transport, and use of sensing bacterial cells adapted to a microcentrifugal microfluidics platform. The microfluidic platform can comprise a structure of low microliter to nanoliter-volume reservoirs connected by micrometer-dimension channels manufactured, for example, by computer numerical control (CNC) machining. An exemplary embodiment of a microfluidic platform 10 is shown in FIG. 7A. In some embodiments, the platform 10 comprises a poly(methyl methacrylate) (PMMA) substrate and has a disk-shape similar to that of a compact disk (CD). With reference to FIG. 7B, the force used for pumping solutions from reservoirs 12 and 14 through reservoir channels 16 and 18 in flow communication with reservoirs 12 and 14, respectively, is a centrifugal force exerted on the fluids when the disk platform 10 is spun on a rotor. The rpm at which a solution will flow from a given reservoir 12 or 14 into a reservoir channel 16 or 18 can be controlled by the size of a burst valve 13 or 15 positioned at the juncture of the reservoirs 12 and 14 and the reservoir channels 16 and 18. Surface tension and fluid/substrate interactions can effectively trap a flowing fluid where a reservoir 12 or 14 meets a burst valve 13 or 15 until these forces are overcome by sufficient centrifugal force.

The reservoirs 12 and 14 can be sealed and one or both can comprise the presently-disclosed biosensors in a vegetative cell (metabolically active) or spore form (metabolically inactive) in a liquid formulation. Liquid can be added in advance and sealed in the reservoirs 12 and 14, or added just prior to addition of centrifugal force. When the microfluidic platform 10 is spun, the biosensors are forced from the reservoir 12 or 14, through the reservoir channels 16 or 18, and into a mixing channel 20 where fluids from each of reservoirs 12 and 14 are mixed with each other, and if desired, other reagents. The biosensor and potentially other reagents mixed together pool in a detection chamber 22 and are exposed to a sample potentially comprising an analyte of interest, either immediately or after an incubation period (e.g., to allow for germination of spore biosensors). If desired, different reservoirs can contain different biosensors.

In one particular embodiment, for example, an aliquot (e.g., 15-20 uL) of the biosensors suspended in water in spore form are stored in a first reservoir (e.g., reservoir 12) and an aliquot (e.g., 15-20 uL) of growth medium (e.g., Luria Bertani (LB) growth medium with our without additional nutrients to enhance sporulation, including amino acids (e.g., L-alanine), sugars (e.g., glucose), and nucleic acids) is stored in a second reservoir (e.g., reservoir 14). In some embodiments, the spore form of the biosensor can first be treated with heat to initiate sporulation (e.g., 65° C. for 15 minutes), with or without additional sporulation promoters. Upon spinning CD platform 10, the biosensor spores and growth medium are released from the two different reservoirs 12 and 14, respectively, pass through reservoir channels 16 and 18, respectively, mix passing through mixing channel 20, and pass into detection chamber 22. The spores germinate in the presence of growth medium to generate a vegetative bacterial cell capable of generating a detectable signal in the presence of an analyte of interest in a sample placed in the detection chamber 22.

If desired, the optical density of the suspension (e.g., measured at 600 nm) can be monitored using, for example, a fiber optic system. A progressive increase of the $OD_{600\ nm}$ is observed over time, thus showing that biosensor spores germinate and biosensor metabolically-active bacterial cells grow in the detection chamber 22 of the microfluidics platform 10. The present inventors have demonstrated that the optical density value that the assay is usually performed at can be reached in just 90 minutes after mixing using the presently-disclosed microfluidics CD platform 10, as compared to the conventional 18 hour overnight incubation required for spore germination and cell growth in a flask.

The biosensor bacterial cells in the detection chamber 22 are then exposed to samples (e.g., environmental (such as air or soil) or biological samples), which can comprise one or more analytes of interest. Expression of a reporter molecule by the biosensor cells is indicative of the presence of the analyte, which can be measured by a signal reader. Thus, the entire assay can be performed directly on the microfluidics platform 10. The presently-disclosed system is readily adaptable and provides for on-site testing not only in environmental analysis, but also in biomedical analysis for patient bedside, physician's office, and home-based applications.

Further, in some embodiments of the presently-disclosed subject matter, a method of detecting an analyte of interest is provided. In some embodiments, the method comprises contacting a test sample suspected of containing the analyte of interest with a biosensor disclosed herein comprising a spore-forming bacterial cell and determining whether a detectable signal is produced by the biosensor to thereby detect the analyte of interest. Methods for detecting a signal are well-known in the art, e.g., detecting a fluorescent signal. "Detecting," as the term is used herein, refers to either a refers to a qualitative (e.g., present or not and/or changed or not signal), quantitative (e.g., measurable amount of or change in detectable signal), or both measurement of the signal.

In some embodiments, the test sample is an environmental sample (e.g., soil, water, or air) or a biological sample. The term "biological sample" as used herein refers to a sample that comprises a biomolecule and/or is derived from an animal or plant subject. The biological sample can be utilized for the detection of the presence and/or level of a biomolecule or analyte of interest in the sample. Representative biomolecules include, but are not limited to DNA, RNA, polypeptides, and carbohydrates, as well as chemical compounds that can interact with and potentially modify biological systems. As such, a biological sample can comprise a cell, a group of cells, fragments of cells, or cell products. Any cell, group of cells, cell fragment, or cell product can be used with the methods of the presently-disclosed subject matter. Exemplary biological fluids include but are not limited to blood, plasma, serum, saliva, and urine. In one embodiment, the biological sample comprises blood. Also encompassed within the phrase "biological sample" are biomolecules that are derived from a cell or group of cells.

In some embodiments of the presently-disclosed subject matter, a kit for detecting an analyte of interest is provided. In some embodiments, the kit comprises a biosensor as disclosed herein comprising a spore-forming bacterial cell, or at least one spore that can generate a bacterial cell as disclosed herein, and instructions for using the biosensor.

EXAMPLES

The presently-disclosed subject matter is further illustrated by the following specific but non-limiting examples.
Materials and Methods for the Examples
Reagents. Potassium antimonyl tartrate, sodium arsenate, sodium phosphate (monobasic), sodium arsenite, zinc chloride, tetracycline and erythromycin were purchased from Sigma-Aldrich (Milwaukee, Wis.). Luria Bertani (LB) agar, M9 minimal medium and LB broth were obtained from Difco (Sparks, Md.). DNA primers were purchased from Operon Biotechnologies (Huntsville, Ala.). All chemicals were reagent grade or better and were used as received. All solutions were prepared using deionized, distilled water (Milli-Q Water Purification System, Millipore, Bedford, Mass.). The chemiluminescent substrate for β-galactosidase, Galacton-light plus, and light emission accelerator-II, a luminescence enhancer reagent, were purchased from Tropix (Bedford, Mass.), and used as suggested by the manufacturer.

Plasmids and bacterial strains. *Bacillus subtilis* strain ars-23 contains plasmid pMUTin-23 bearing a set of 3 genes that confer resistance to arsenic (arsR, arsB, arsC) along with the reporter gene lac-Z encoding β-galactosidase under control of the ArsR regulatory protein (FIG. 1).[21] ArsR is a DNA-binding repressor protein that regulates the expression of the ars operon. Upon binding As (III), ArsR releases itself from its DNA binding site, thus permitting gene transcription. ArsB is a membrane protein that pumps As (III) out of the cell using the electrochemical gradient across the membrane as the energy source. ArsC is a small cytoplasmic protein that reduces As (V) to As (III). For more details on the detoxification system encoded by the ars operon, see the review article by Daunert et al.[1]

The plasmid pSD202 (FIG. 1) was prepared by inserting a Kpnl-Sphl fragment containing the egfp and smtB genes between the Kpnl-Sphl sequences of plasmid pMM1522 (Mobitec, Boca Raton, Fla.). The egfp gene, encoding the enhanced green fluorescent protein (EGFP), was isolated from plasmid pEGFP (Clontech, Mountainview, Calif.) using PCR. Similarly, the sequences of the O/P and smtB gene of the *Synechococcus* PCC7942 smt operon were isolated from plasmid pJLE3C.[22] The smtB gene codes for a zinc-binding protein that regulates expression of the smt operon. SmtB is a repressor protein that, upon binding zinc, unbinds itself from the O/P region, thus allowing expression of the smtA gene, which is under the promoter control. The smtA gene codes for the SmtA protein, a metallothionein that binds zinc. The protein-bound metal is either transported within the cell for use by Zn-dependent enzymes, or is sequestered in inclusion bodies. A schematic of the smt operon machinery is shown in FIG. 2. The overlap extension of the two gene fragments was carried out by PCR to create the Kpnl-Sphl fragment containing the egfp and smtB genes. The resulting pSD202 vector contains the O/P region of the smt operon, the smtB gene and the egfp gene placed downstream under control of the smt operon promoter. The construction of the pSD202 plasmid was verified by digesting the plasmid with Kpnl and Sphl and confirming the lengths of the digested fragments on a 1% agarose gel. The plasmid pSD202 was transformed into *Bacillus megaterium* strain *WH*320 cells using conventional protocols (Mobitec, Boca Raton, Fla.).

Bacterial spores. Spores of both types of bacterial sensing cells, i.e., the ars-23 *B. subtilis* strain and the *B. megaterium* strain for zinc constructed in this work, were prepared by using standard protocols and media, as described elsewhere.[23] Briefly, spores were generated by placing bacterial cells in sporulation medium at 37° C. with vigorous shaking for 4 days. All spores were harvested by centrifugation at 10,000×g for 10 min at 4° C., washed twice, and resuspended in deionized distilled water. Spore suspensions were then sonically vibrated for 5 min using the 550 sonic dismembrator from Fisher Scientific (Pittsburgh, Pa.) to release the endospores from the outer cell wall. Sonicated spore suspensions were centrifuged at 10,000×g for 10 min at 4° C. The supernatant was decanted to remove the outer cell wall debris, and the free spores were resuspended in deionized distilled water at an optical density of 0.8 at 600 nm ($OD_{600}$) and stored at room temperature for various periods of time.

Apparatus. Chemiluminescence and fluorescence measurements were made on a Polarstar Optima microplate luminometer from BMG Labtech (Durham, N.C.). All experiments were conducted at room temperature unless specified otherwise. All luminescence intensities reported are the average of a minimum of three replicates, and are expressed in relative light units (RLU). Spores were observed at different magnifications (3,000× to 8,000×) under a Hitachi S-3200 scanning electron microscope at the University of Kentucky electron microscopy facility.

Dose-response curves for antimonite, arsenate, and arsenite. A single colony of *B. subtilis* ars-23 strain or a volume of 20 μL of spore suspension was added to 300 mL of LB broth containing erythromycin (50 μg/mL). Bacterial cells from colony and spores were grown overnight at 37° C., 250 rpm until the $OD_{600}$ reached 0.6-0.7. Aliquots of 1 mL of bacterial suspension were then transferred into culture tubes. Analyte standard solutions of concentrations ranging from $1\times10^{-4}$ M to $1\times10^{-9}$ M were prepared in deionized, distilled water by serial dilutions of freshly prepared $1\times10^{-2}$ M stock solutions of potassium antimonyl tartrate, sodium arsenate, and sodium arsenite, respectively. A volume of 200 μL of each of these standard solutions and deionized, distilled water as blank was added in triplicate to the culture tubes containing the cell suspension. These culture tubes were then incubated at 37° C. at 250 rpm for 1 h. Next, bacterial suspensions were centrifuged at 8000×g for 5 min at 4° C. The pelleted cells were washed with 100 mM phosphate buffer, pH 7.4, then resuspended in 1 mL of the same buffer containing 0.2% (w/v) Triton-X-100, and placed in a shaker at 37° C. at 250 rpm for 1 h in order for the reporter enzyme β-galactosidase to be released into the medium after cell lysis. A 30 μL volume of cell lysate was added to 100 μL of chemiluminescent substrate solution and incubated in a 37° C. shaker at 250 rpm for 1 h. The chemiluminescence signal was triggered by injecting 100 μL of accelerator-II solution into the substrate-enzyme mixture. After a delay of 20 s necessary to reach maximal light emission, the chemiluminescent signal was collected over a period of time of 3 s on the microplate luminometer.

Dose-response curves for zinc. A single colony or a volume of 20 μL of spore suspension of the *B. megaterium* strain bearing the reporter plasmid pSD202 was grown overnight at 37° C. in a culture tube containing 5 mL of LB broth and tetracycline (20 μg/mL). When the $OD_{600}$ reached 0.7-0.8, the bacteria were transferred into a 500-mL flask containing 100 mL of LB broth and tetracycline (20 μg/mL) and grown at 37° C. until the $OD_{600}$ reached 0.8. The bacterial cells were then centrifuged at 6000 rpm at 4° C. for 5 min and the supernatant was discarded. The cells were washed twice with 10 mL of M9 minimal salt medium, then resuspended in M9 medium supplemented with $CaCl_2$ and $MgSO_4$ and 10% glucose until an $OD_{600}$ of 0.8 was obtained. Aliquots of 1.8 mL of cell suspension were transferred into culture tubes. Zinc standard solutions ranging from $1\times10^{-4}$ M to $1\times10^{-7}$ M were prepared in deionized, distilled water by serial dilution starting with a $1\times10^{-2}$ M solution of zinc chloride. A volume of 200 μL of each of these standard solutions and deionized, distilled water as blank was added in triplicate to the culture tubes containing the cell suspension. After incubation for 1 h, the cells were harvested by centrifugation at 6,000 rpm for 5 min at 4° C. The supernatant was discarded, while the cells were washed twice with 100 mM phosphate buffer, Ph 7.5, and resuspended in 500 μL of the same buffer. Subsequently, a volume of 100 μL of cell suspensions was diluted to 1 mL with the same buffer in glass tubes. A volume of 200 μL of these diluted cell suspensions was transferred in triplicate into a 96-well microtiter plate. The fluorescence measurements were carried out in the microplate luminometer with excitation wavelength set at 480 nm and emission wavelength at 510 nm.

Selectivity studies. The selectivity of *B. subtilis* strain ars-23 was evaluated by incubating the sensing cells with $1\times10^{-4}$ M solutions of potassium antimonyl tartrate, sodium arsenate, sodium arsenite, potassium ferricyanide, potassium dichromate, and sodium sulfate. Similarly, the selectivity of the *B. megaterium* strain for zinc developed in this work was evaluated by incubating the sensing cells with $1\times10^{-4}$ M solutions of zinc chloride, cobalt chloride, nickel chloride and cadmium chloride. In both cases, the assay was performed as described above.

Results and Discussion for Examples

Whole-cell sensing systems have been employed for the detection of a variety of analytes. Their selectivity/specificity and sensitivity characteristics have made them an attractive tool for a number of analytical applications. In order for these biosensing systems to find practical on-site applications, they need to be incorporated into devices. For that, the present inventors have developed cells, systems, and methods based on the use of spore-forming bacteria, which provides reliable and inexpensive means of maintenance, storage and transport of the bacterial sensing systems, and which can facilitate the integration of living cells into portable analytical devices.

As exemplary models of the broad applicability of this spore-based approach, the inventors have developed two distinct sensing systems for the detection of arsenic and zinc, respectively, which employ different reporter genes and different *Bacillus* species as the host microorganism. Arsenic is a well-characterized environmental contaminant with toxic effects on humans that lead to vascular diseases, dermatitis, and cancer.[24] Zinc is an essential element whose deficiency is responsible for decreased growth rate and mental development in infants, impaired wound healing and immune function, and reproductive failure, among others.[25]

Figure 1:
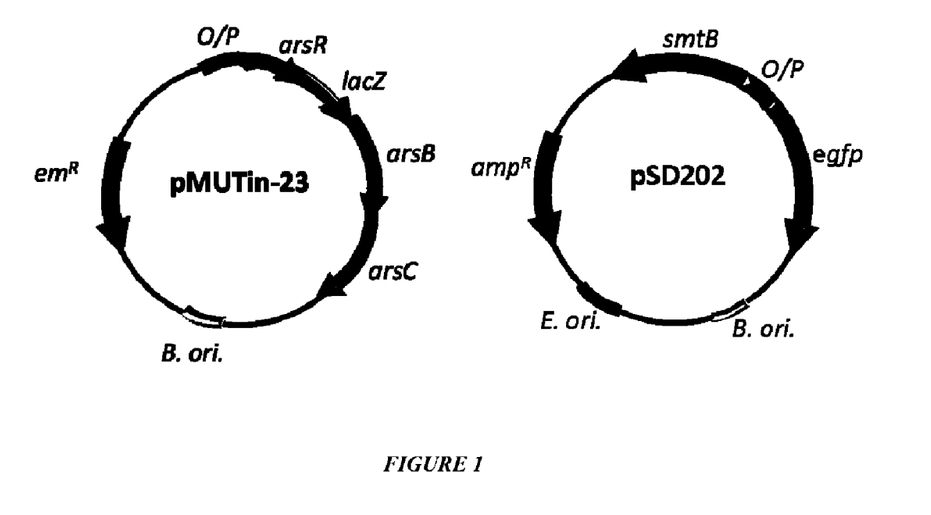
FIG. 1 is a schematic of the plasmids pMUTin-23 and pSD202 employed for arsenic and zinc sensing, respectively.
Figure 2:
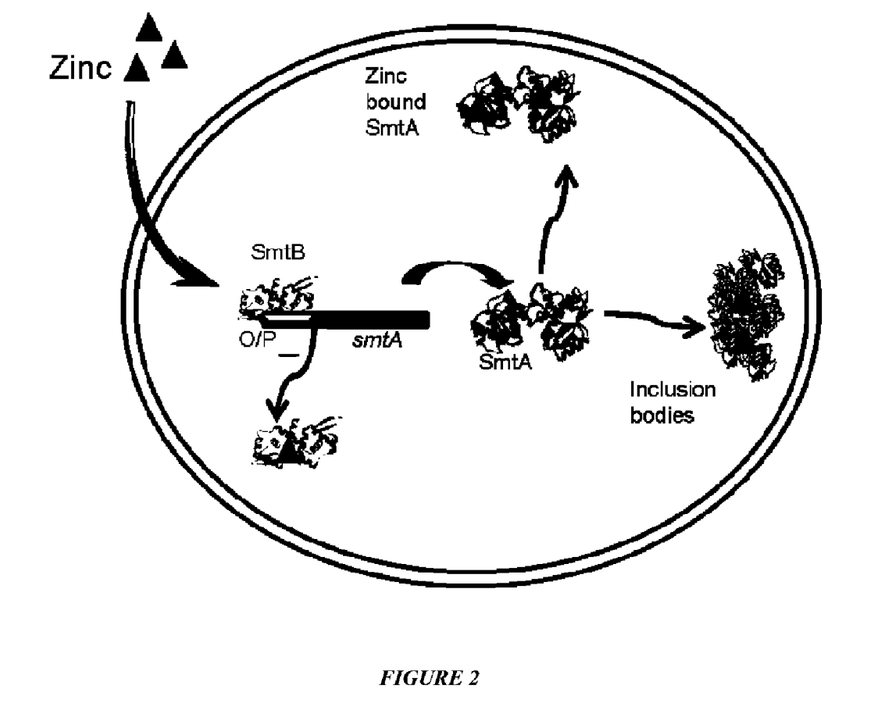
FIG. 2 is a schematic of the machinery of the smt operon in *Synechococcus* PCC7942.

Specifically, the *Bacillus subtilis* strain ars-23 contains a plasmid bearing lac-Z, the gene encoding the reporter enzyme β-galactosidase, fused in-frame to part of the ORF2 gene, downstream of the arsR gene of the *Bacillus subtilis* ars operon.[19] The other genes of the ars operon, arsB and arsC, are located downstream of the lac-Z gene (FIG. 1). The β-galactosidase reporter protein catalyzes the hydrolysis of β-galactosides. In these Examples, the activity of the β-galactosidase enzyme was monitored by using a chemiluminescent substrate, a 1,2-dioxetane β-D-galactopyranoside derivative. The enzymatic reaction results in the emission of light at 463 nm in a manner that is directly proportional to the concentration of bioavailable analyte, in this case, arsenite or antimonite, present in the sample.

The first step in the analytical characterization of this bacterial strain was to demonstrate that the *Bacillus* cells were capable of sensing. For that, the cells were incubated with varying concentrations of sodium arsenite and potassium antimonyl tartrate in the conditions described above. Since the genetic construct employed in the Examples includes arsC, a gene encoding the ArsC protein that functions as arsenate reductase to reduce arsenate to arsenite, the sensing cells were also incubated with varying concentrations of sodium arsenate. The β-galactosidase expressed by the bacteria in response to the analyte intracellular amount could be related to the extracellular concentration of analyte. Dose-response curves were constructed, thus showing that the *Bacillus* cells could sense all of the three analytes in a dose-dependent fashion. The ability of responding to, both, arsenite and arsenate is important for the analysis of many samples, where different species of arsenic could be present.

The detection limits for antimonite, arsenate and arsenite were found to be $2.8 \times 10^{-8}$ M, $1.6 \times 10^{-7}$ M, and $2.8 \times 10^{-7}$ M, respectively, with dynamic ranges over 2 to 3 orders of magnitude. The detection limit was defined as the analyte concentration that produced a signal equal to or higher than the average signal produced by the blank plus three standard deviations.

The intra- and inter-assay reproducibility was satisfactory, as shown by values of the coefficients of variation ranging 4-14%. Selectivity studies were also performed with the *B. subtilis* ars-23 strain. Cells were treated with $1 \times 10^4$ M solutions of sodium sulphate, potassium ferricyanide, potassium dichromate, and sodium arsenite, respectively, and the resulting chemiluminescence was measured.

The results showed that the response to ions with size, charge, and structure similar to that of antimonite/arsenite was negligible when compared to the response to the target analytes, thus confirming the selectivity of the sensing strain. Overall, the analytical performance of the *Bacillus*-based sensing system (Table 1) proved to be consistent with that of other sensing systems developed for arsenic using the same reporter gene and non-sporulating bacteria, such as *Escherichia coli*, as the host microorganism.[11]

In order to develop a bacterial sensing system for zinc, plasmid pSD202 was designed to incorporate the gene for the reporter protein eGFP under transcriptional control of the promoter and the regulatory protein SmtB of the smt operon (FIG. 1). The smtB gene is placed upstream while the egfp gene is located downstream of the O/P region of the smt operon. In the absence of zinc ions, the SmtB protein binds to the O/P region of the smt operon and inhibits the transcription of the eGFP protein. Alternatively, the presence of zinc ions, which bind to SmtB, causes a conformational change in the SmtB protein that leads to transcription of the egfp gene located downstream of the O/P region.

After transformation of the reporter plasmid pSD202 into *Bacillus megaterium*, the bacterial cells were incubated with varying concentrations of zinc chloride, and the signal produced by the eGFP expressed by the bacteria was measured to evaluate their response. A dose-dependent response was observed in a range of concentrations over 2 orders of magnitude, with a detection limit for zinc of $1 \times 10^{-6}$ M.

Figure 3:
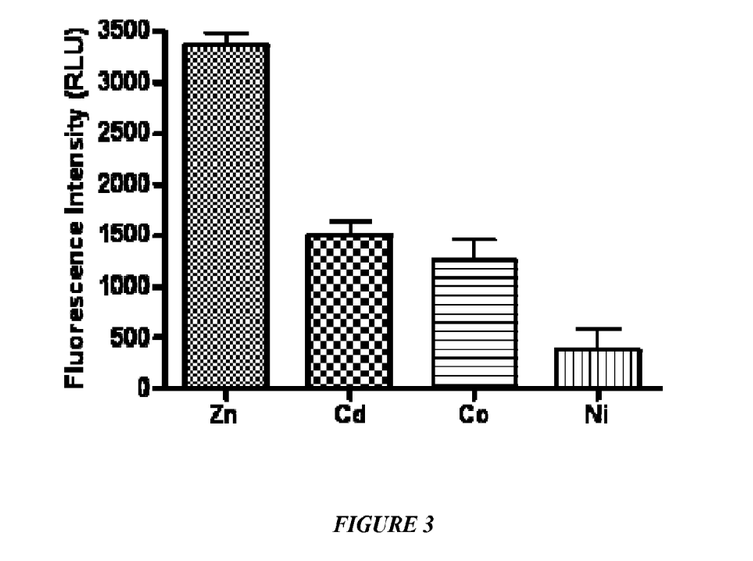
FIG. 3 is a graph showing data from a selectivity study performed with *B. megaterium* cells harboring plasmid pSD202. Cells were incubated for 1 h at 37° C. with a 1×10 M solution of each ion and the resulting fluorescence intensity was measured with $\lambda_{ex}$ of 480 nm and a $\lambda_{em}$ of 510 nm. The signals have been corrected with respect to the blank. Data are the average±one standard deviation (n=3).

Reproducibility studies exhibited intra- and inter-assay coefficient of variation values below 14%. Selectivity studies were also performed with *B. megaterium* WH130 cells harboring plasmid pSD202. Cells were treated with $1 \times 10^{-4}$ M solutions of $Cd^{2+}$, $Ni^{2+}$, and $Co^{2+}$ ions, respectively, and the resulting fluorescence intensity was measured. It was observed that the biosensor also responded to these ions, although the response was less than that to $Zn^{2+}$ ions, as reported in FIG. 3. In fact, the SmtB protein is also known to be responsive to $Cd^{2+}$ and $Co^{2+}$ because of its sequence similarity to other metalloregulatory proteins, such as CadC.[26] The sensor's ability of responding to $Cd^{2+}$ should not interfere with $Zn^{2+}$ sensing in biological fluids because cadmium is a toxic heavy metal not expected to be found in humans at significant levels, unless accidental exposure occurred. On the other hand, cobalt is an essential element present in the human body as a constituent of vitamin $B_{12}$. However, cobalt blood levels are reported to be in the order of nanomolar concentrations, which are at least three orders of magnitude lower than optimal zinc blood levels ($1.2 \times 10^{-5}$-$3.8 \times 10^{-5}$ M).[27]

Figure 4:
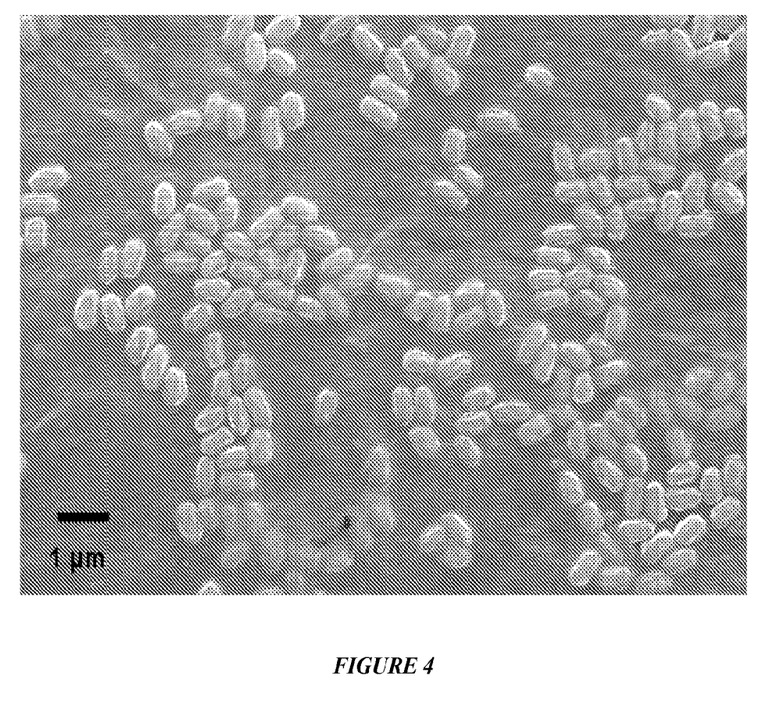
FIG. 4 is a scanning electron micrograph of spores of *B. subtilis*. Magnification 4500×. Scale bar represents 1 μm.
Figure 5:
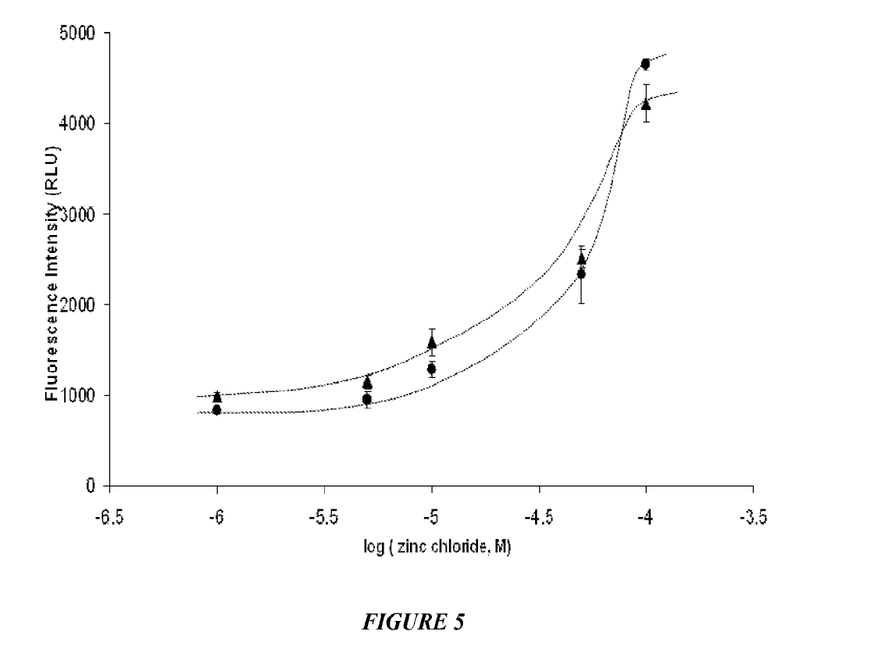
FIG. 5 is a graph showing dose-response curves of the *B. megaterium* sensing cells harboring the pSD202 plasmid, generated before (□) and after (Δ) sporulation. Cells were incubated with various concentrations of zinc chloride for 1 h at 37° C. Fluorescence intensity was measured with a $\lambda_{ex}$ of 480 nm and $\lambda_{em}$ of 510 nm. The signals have been corrected with respect to the blank. Data are the average±one standard deviation (n=3).

After evaluating the analytical performance of the developed whole-cell sensing systems, cells of *B. subtilis* containing arsR-lac-Z genes and of *B. megaterium* containing smtB-egfp genes were sporulated following standard sporulation protocols as described in the Experimental Section. A scanning electron micrograph of the spores thus obtained, at a magnification of 4500×, is shown in FIG. 4. The size of spores was determined to be approximately 1 μm by 0.5 μm. A spore is composed of a set of protective structures arranged in series of concentric shells. The DNA is stored in a desiccated form within the core of the structure. DNA stored in such a manner can be preserved for long periods of time without any special requirements. When provided with the essential germinating agents and nutrients, spores can germinate and regain complete cellular activities. Upon these considerations, spores of each of the two biosensing systems were exposed to germination conditions and the obtained vegetative cells were then evaluated for their ability to respond to the respective analytes, by using the protocols described above. The results for both sensing systems indicated that, not only were the germinated cells responsive to the analytes in a dose-dependent fashion, but they also maintained their analytical performance in terms of detection limit, dynamic range and reproducibility. A representative example for the zinc biosensor is shown in FIG. 5.

Figure 6:
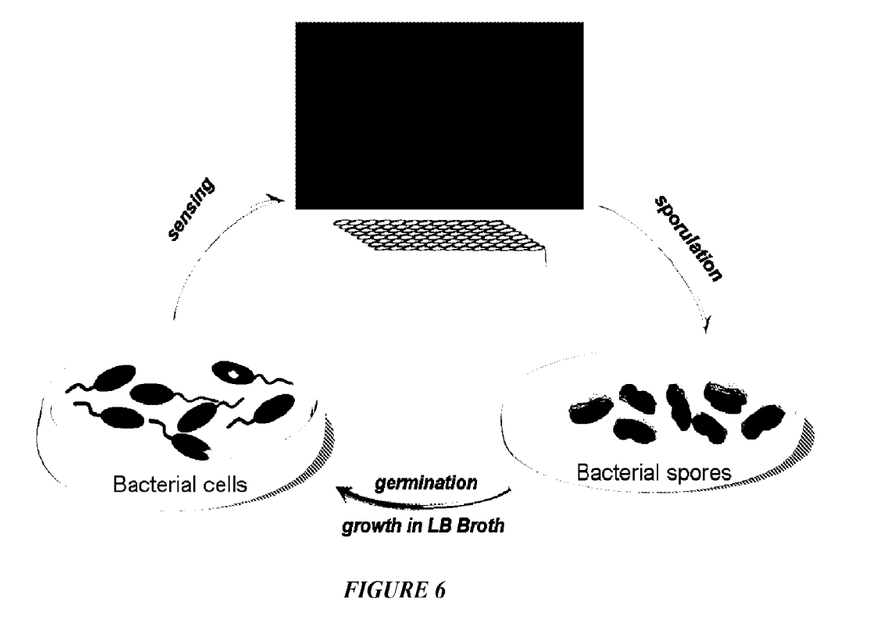
FIG. 6 is a schematic representation of the experimental setup including sensing-sporulation-germination cycles.

The sustainability of spores as a means for preserving, storing, and transporting whole-cell sensing systems was further evaluated by exposing the sensing bacteria to three sporulation-germination cycles at intervals of 1 month. The detection limits and dynamic ranges for the analytes, as well as the reproducibility of the spore-based biosensing systems, were determined after germination in each cycle. A schematic of the experimental set-up is presented in FIG. 6. The results obtained in these sets of experiments are summarized in Table 1 for the antimonite/arsenate/arsenite biosensor, and in Table 2 for the zinc biosensor. It is evident that, both limits of detection and dynamic ranges did not change significantly after each sporulation-germination cycle, with comparison to pre-sporulation. Of particular interest, both of the spore-based sensing systems retained their analytical performance also after being stored at room temperature for at least six months and eight months, respectively, thus supporting the long-term storage of the sensing bacterial cells in the form of spores. Follow-on data determined that the ArsR retained the analytical performance for two years, further supporting the long-term storage capability of the presently-disclosed biosensor systems.

The coefficients of variation were also consistent with those calculated before sporulation, thus confirming the reproducibility of the system over time, and after sporulation/germination cycles. It is noteworthy that, along with the performance being virtually identical before and after sporulation, the cell's response in terms of signal intensity is also virtually identical (FIG. 5). These results show that the reported spore-based approach allows addressing one of the most relevant drawbacks of whole cell sensing systems, that is, their limited stability.

The use of spores as biosensors in an effective packaging method for the storage and transport of sensing bacterial cells has also been adapted into a system comprising a portable microcentrifugal microfluidics platform as disclosed herein (FIGS. 7A and 7B) in order to further enhance the on-site employment of spore-based whole-cell sensing systems. The microfluidics device utilized for the present examples is shown in FIGS. 7A and 7B and comprises a structure of low microliter to nanoliter-volume reservoirs connected by micrometer-dimension channels manufactured by computer numerical control (CNC) machining. It can be made of a poly(methyl methacrylate) (PMMass.) substrate and has a disk-shape similar to that of a Compact disk (CD) (FIG. 7A). The force used for pumping solutions in the reservoirs through the channels is a centrifugal force exerted on the fluids when the disk is spun on a rotor. The rpm at which a solution will flow from a given reservoir into a channel can be controlled by the size of a burst valve. Surface tension and fluid/substrate interactions can effectively trap a flowing fluid where a chamber meets a burst valve until these forces are overcome by sufficient centrifugal force. This platform can be easily transported and operated in situ using a typical CD reader. Spore germination and bacterial cell growth has been achieved on the microfluidics platform disclosed herein, and it has been demonstrated that the optimal optical density value for the cell suspension was reached in 90 minutes on the CD, compared to the overnight incubation required when employing conventional methods.

Figure 8:
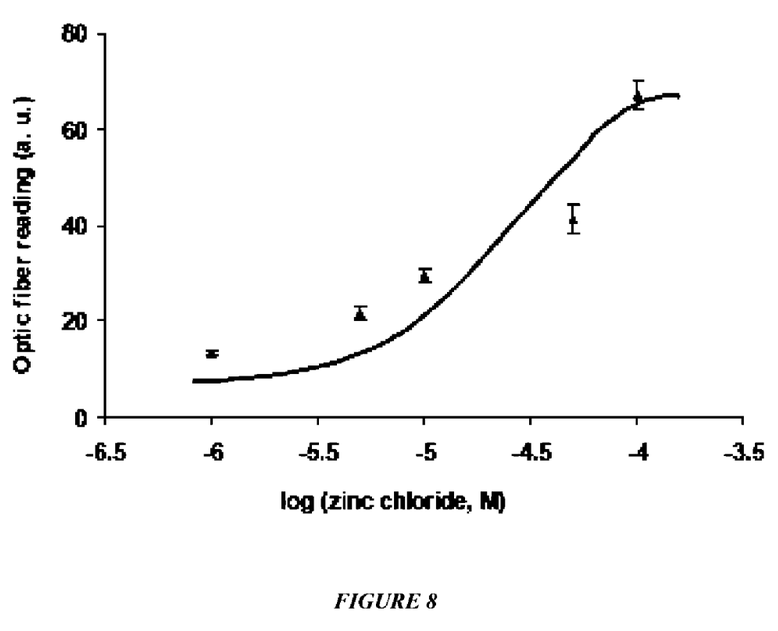
FIG. 8 is a graph showing Zinc sensing on the microfluidics CD platform disclosed herein.

*B. megaterium* recombinant cells and zinc sensing have been incorporated in the miniaturized microfluidics platform. Upon CD spinning, a 17-μl aliquot of sensing bacterial cells suspended in Luria Bertani (LB) growth medium and 17 μl of zinc chloride solutions at various concentrations were released from two different reservoirs and mixed into the detection chamber, where the fluorescence signal was monitored by a fiber optic system. Sensing was successfully performed in the CD, thus allowing for the rapid (10 min) detection of zinc at low μM levels in low μL volume samples (FIG. 8).

Conclusions

As demonstrated by the Examples, the presently-disclosed subject matter provides a new method of preservation, storage and transport of whole cell biosensing systems based on the formation of spores that allows for their broad use in on-site applications, thus circumventing some of the current drawbacks of cell-based biosensors. Furthermore, the possibility of long-term storage of the whole-cell sensing systems enables their incorporation into various analytical devices such as micro-total analytical systems (μ-TAS) by packaging them with all the needed reagents in a dry form. This can further facilitate environmental on-field applications, as well as biomedical applications at the patient bedside and the physician's office. The use of miniaturized analytical systems also allows for incorporating multiple biosensing systems in one small device, thus providing with a portable solution to environmental and clinical multiplexed, on-site analysis. Moreover, the well-documented resistance of spores to extreme conditions such as dry and wet heat, freezing temperatures, and desiccation, among others, can provide for the use of whole-cell sensing systems in harsh environments, upon evaluation of the stability of the spore-based whole-cell sensing systems in those environments. This is of particular importance in developing countries, which often experience difficult environmental conditions and have poor storage and transportation facilities, or in the challenging environments of a battlefield.

TABLE 1

Analytical characteristics of the spore-based whole-cell sensing system for antimonite/arsenate/arsenite evaluated before sporulation and after several sporulation/germination cycles, as well as after long-term storage of the spores. The limit of detection was defined as the analyte concentration that produced a signal equal to or higher than the average signal produced by the blank plus three standard deviations.

| Analyte | Before Sporulation | Cycle 1 | Cycle 2 | Cycle 3 | After 6 Months Storage |
|---|---|---|---|---|---|
| Detection Limit (M) | | | | | |
| Antimonite | $2.8 \times 10^{-8}$ | $1.6 \times 10^{-8}$ | $1.6 \times 10^{-8}$ | $2.8 \times 10^{-8}$ | $1.6 \times 10^{-8}$ |
| Arsenate | $1.6 \times 10^{-7}$ | $1.6 \times 10^{-8}$ | $2.8 \times 10^{-7}$ | $1.6 \times 10^{-7}$ | $2.8 \times 10^{-7}$ |
| Arsenite | $2.8 \times 10^{-7}$ | $1.6 \times 10^{-7}$ | $2.8 \times 10^{-7}$ | $2.8 \times 10^{-7}$ | $2.8 \times 10^{-7}$ |
| Dynamic Range (M) | | | | | |
| Antimonite | $1.6 \times 10^{-5}$-$2.8 \times 10^{-8}$ | $1.6 \times 10^{-5}$-$1.6 \times 10^{-8}$ | $1.6 \times 10^{-5}$-$1.6 \times 10^{-8}$ | $1.6 \times 10^{-5}$-$1.6 \times 10^{-8}$ | $2.8 \times 10^{-5}$-$1.6 \times 10^{-8}$ |
| Arsenate | $2.8 \times 10^{-5}$-$1.6 \times 10^{-7}$ | $8.3 \times 10^{-5}$-$1.6 \times 10^{-7}$ | $1.6 \times 10^{-4}$-$2.8 \times 10^{-7}$ | $1.6 \times 10^{-4}$-$2.8 \times 10^{-7}$ | $2.8 \times 10^{-4}$-$2.8 \times 10^{-7}$ |
| Arsenite | $1.6 \times 10^{-5}$-$2.8 \times 10^{-7}$ | $1.6 \times 10^{-4}$-$1.6 \times 10^{-7}$ | $1.6 \times 10^{-4}$-$2.8 \times 10^{-7}$ | $1.6 \times 10^{-4}$-$2.8 \times 10^{-7}$ | $1.6 \times 10^{-5}$-$2.8 \times 10^{-7}$ |

TABLE 2

Analytical characteristics of the spore-based whole-cell sensing system for zinc evaluated before sporulation and after several sporulation/germination cycles, as well as after long-term storage of the spores. The limit of detection was defined as the analyte concentration that produced a signal equal to or higher than the average signal produced by the blank plus three standard deviations.

| | Detection Limit (M) | Dynamic Range (M) |
|---|---|---|
| Before Sporulation | $1 \times 10^{-6}$ | $1 \times 10^{-4}$-$1 \times 10^{-6}$ |
| Cycle 1 | $1 \times 10^{-6}$ | $1 \times 10^{-4}$-$1 \times 10^{-6}$ |
| Cycle 2 | $1 \times 10^{-6}$ | $1 \times 10^{-4}$-$1 \times 10^{-6}$ |
| Cycle 3 | $1 \times 10^{-6}$ | $1 \times 10^{-4}$-$1 \times 10^{-6}$ |
| After 8 Months Storage | $1 \times 10^{-6}$ | $1 \times 10^{-4}$-$1 \times 10^{-6}$ |

One of ordinary skill in the art will recognize that modifications and variations are possible without departing from the teachings of the presently-disclosed subject matter. This description, and particularly the specific details of the exemplary embodiments disclosed, is provided primarily for clearness of understanding and no unnecessary limitations are to be understood therefrom, for modifications and other embodiments will become evident to those skilled in the art upon reading this disclosure and may be made without departing from the spirit or scope of the claimed invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that can vary depending upon the desired properties sought to be determined by the presently-disclosed subject matter.

Notwithstanding that the numerical ranges and parameters setting forth the broad scope of the present subject matter are approximations, the numerical values set forth in the example sections are reported as precisely as possible. Any numerical value, however, inherently contains certain errors necessarily resulting from the standard deviation found in their respective testing measurements.

References

Throughout this application, various publications are referenced. All such references are incorporated herein by reference, including the references set forth in the following list:

1. Daunert, S.; Barrett, G.; Feliciano, J. S.; Shetty, R. S.; Shrestha, S.; Smith-Spencer, W. *Chem. Rev.* 2000, 100, 2705-2738.
2. Belkin, S. *Curr. Opin. Microbiol.* 2003, 6, 206-212.
3. Gu, M. B.; Mitchell, R. J.; Kim, B. C. *Adv. Biochem. Engin./Biotechnol.* 2004, 87, 269-305.
4. Standing, D.; Meharg, A. A.; Killham, K. A. *FEMS Microbial. Lett.* 2003, 220, 35-39.
5. Kumari, A.; Pasini, P.; Deo, S. K.; Flomenhoft, D.; Shashidhar, H.; Daunert, S. *Anal. Chem.* 2006, 78, (22), 7603-7609.
6. Feliciano, J.; Pasini, P.; Deo, S. K.; Daunert, S., Photoproteins as reporters in whole-cell sensing. In *Photoproteins in Bioanalysis*, Daunert, S.; Deo, S. K., Eds. Wiley VCH: Weinheim, 2006; pp 131-154.
7. Galluzzi, L.; Karp, M. Comb. Chem. *High Throughput Screen.* 2006, 9, (7), 501-14.
8. Yagi, K. *Appl. Microbiol. Biotechnol.* 2007, 73, 1251-1258.
9. Harms, H.; Wells M. C.; van der Meer J. R. *Appl. Microbial. Biotechnol.* 2006, 70, 273-80.
10. Sorensen, S. J.; Burmolle, M.; Hansen L. H. *Curr. Opinion. Biotechnol.* 2006, 17, 11-16.
11. Turner, K.; Xu, S.; Pasini, P.; Daunert, S. *Anal. Chem.* 2007, published on web Jun. 30, 2007.
12. Shetty, R. S.; Deo, S. K.; Liu, Y.; Daunert S. *Biotechnol. Bioeng.* 2004, 88, (5), 66470.
13. Ramanathan, S.; Shi, W.; Rosen, B. P.; Daunert, S. *Anal. Chim. Acta* 1998, 369, 189-95.
14. Stocker, J.; Balluch, D.; Gsell, M.; Harms, H.; Feliciano, J.; Daunert, S.; Malik, K. A.; van der Meer J. R. *Environ. Sci. Technol.* 2003, 37, (20), 4743-50.
15. Premkumar, J. R.; Rosen, R.; Belkin, S.; Lev, O. *Anal. Chim. Acta* 2002, 462, 11-23.
16. Polyak, B.; Bassis, E.; Novodvorets, A.; Belkin, S.; Marks, R. S. *Sens. Actuators B Chem.* 2001, 74, 18-26.
17. Mbeunkui, F.; Richaud, C.; Etienne, A.; Schmid, R. D.; Bachmann, T. T. *Appl. Microbiol. Biotechnol.* 2002, 60, 306-312.

18. Bjerketorp, J.; Hakansson, S.; Belkin, S.; Jansson J. *Curr. Opin. Biotechnol.* 2006, 17, 43-49.
19. Nicholson, W. L. *Cell. Mol. Life. Sci.* 2002, 59, 410-416.
20. Moir, A.; Corfe, B. M.; Behravan, *J. Cell. Mol. Life. Sci.* 2002, 59, 403-409.
21. Sato, T.; Kobayashi, Y. *J. Bacteriol* 1998, 180, 1655-1661.
22. Erbe, J. L.; Taylor, B.; Hall, L. M. *Nucleic Acids Res.* 1995, 23, 2472-2478.
23. Harwood C. R. Cutting S. M. *Molecular biological methods for Bacillus*. Wiley, N.Y. 1990.
24. Abernathy, C. O.; Liu, Y.; Longfellow, D.; Aposhian, H. V.; Beck, B.; Fowler, B.; Goyer, R.; Menzer, R.; Rossman, T.; Thomson, C.; Waalkes, M. *Environ. Health Perspect.* 1999, 107, 593-97.
25. Black, M. M. *J. Nutr.* 2003, 133, 1473-76.
26. Turner, J. S.; Glands, P. D.; Samson, A.; Robinson, N. *J. Nucleic Acids Res.* 1996, 24, 3714-3721.
27. Zapsalis, C.; Beck, R. A. *Food Chemistry and Nutritional Biochemistry*, Wiley: N.Y.; 1985

What is claimed is:

1. A biosensor, comprising:
   (a) a spore-forming bacterial cell, wherein the cell can generate one or more spores capable of being germinated to thereby reproduce the spore-forming bacterial cell, and wherein the cell is provided in spore form;
   (b) a recognition element within the spore-forming bacterial cell for binding an analyte of interest; and
   (c) a reporter molecule within the spore-forming bacterial cell for detecting binding of the analyte of interest, wherein the reporter molecule generates a detectable signal upon binding of the analyte by the recognition element.

2. The biosensor of claim 1, wherein the spore-forming bacterial cell is a *Bacillus* sp. bacterial cell or a *Clostridium* sp. bacterial cell.

3. The biosensor of claim 2, wherein the spore-forming bacterial cell is *Bacillus subtilis* or *Bacillus megaterium*.

4. The biosensor of claim 1, wherein the spore-forming bacterial cell is a transformed bacterial cell.

5. The biosensor of claim 4, wherein the bacterial cell comprises a heterologous polynucleotide expression cassette comprising a promoter operatively linked to a nucleotide sequence encoding the reporter molecule.

6. The biosensor of claim 5, wherein the recognition element is a regulatory peptide having binding affinity for the promoter, and wherein the regulatory peptide binds the promoter and inhibits expression of the reporter molecule.

7. The biosensor of claim 6, wherein binding of the analyte of interest by the regulatory peptide releases binding of the regulatory peptide to the promoter, thereby allowing expression of the reporter molecule and generation of the detectable signal.

8. The biosensor of claim 6, wherein the regulatory peptide comprises an ArsR peptide, an SmtB peptide, an HbpR peptide, an AraC peptide, or a functional fragment thereof.

9. The biosensor of claim 5, wherein the expression cassette is a plasmid selected from the group consisting of pMU-Tin-23 and pSD202.

10. The biosensor of claim 1, wherein the reporter molecule comprises a peptide selected from the group consisting of β-galactosidase and green fluorescent protein.

11. The biosensor of claim 1, wherein the analyte of interest is a toxic compound or a biomolecule.

* * * * *